United States Patent [19]

Sato et al.

[11] Patent Number: 4,929,539
[45] Date of Patent: * May 29, 1990

[54] SILVER HALIDE PHOTOSENSITIVE MATERIALS FOR COLOR PHOTOGRAPHY

[75] Inventors: Ryosuke Sato; Katsunori Kato; Takashi Sasaki; Hiroshi Sugita, all of Tokyo, Japan

[73] Assignee: Konishiroku Photo Industry Co., Ltd., Tokyo, Japan

[*] Notice: The portion of the term of this patent subsequent to May 29, 2001 has been disclaimed.

[21] Appl. No.: 191,224

[22] Filed: May 6, 1988

Related U.S. Application Data

[60] Division of Ser. No. 540,720, Oct. 11, 1983, Pat. No. 4,772,542, which is a division of Ser. No. 522,818, Aug. 12, 1983, Pat. No. 4,451,559, which is a continuation of Ser. No. 385,096, Jun. 4, 1982, abandoned.

[30] Foreign Application Priority Data

Jun. 11, 1981 [JP] Japan .................................. 56-90334
Jun. 11, 1981 [JP] Japan .................................. 56-90335
Jun. 11, 1981 [JP] Japan .................................. 56-90336

[51] Int. Cl.$^5$ .................................. G03C 7/34
[52] U.S. Cl. .................................. 430/553; 430/552
[58] Field of Search .................................. 430/552, 553

[56] References Cited

U.S. PATENT DOCUMENTS

| | | | |
|---|---|---|---|
| 3,446,622 | 5/1969 | Magagnoli et al. | 430/552 |
| 3,758,308 | 9/1973 | Beavers et al. | 430/553 |
| 3,772,002 | 11/1973 | Ramello et al. | 430/553 |
| 3,880,661 | 4/1975 | Lau et al. | 430/553 |
| 4,333,999 | 6/1982 | Lau | 430/552 |
| 4,427,767 | 1/1984 | Aoki et al. | 430/553 |
| 4,451,559 | 5/1984 | Sato et al. | 430/553 |
| 4,454,244 | 11/1985 | Sato et al. | 430/553 |
| 4,465,766 | 8/1984 | Sato et al. | 430/553 |
| 4,772,543 | 9/1988 | Sato et al. | 430/553 |

*Primary Examiner*—Richard L. Schilling
*Attorney, Agent, or Firm*—Frishauf, Holtz, Goodman & Woodward

[57] ABSTRACT

There is disclosed a silver halide photosensitive material for color photography which comprises a phenol type cyan coupler having the formula:

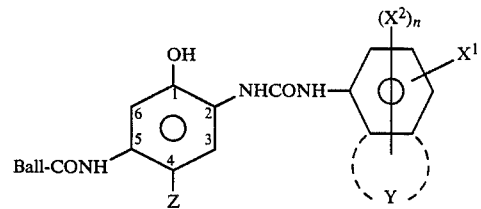

wherein the substituents $X^1$, $X^2$, Y, Z and n are as defined in the specification and claim of this application.

The cyan coupler mentioned above is a novel cyan dye image-forming coupler and the photosensitive material containing the same according to the present invention has removed the various drawbacks in the prior art.

5 Claims, No Drawings

SILVER HALIDE PHOTOSENSITIVE MATERIALS FOR COLOR PHOTOGRAPHY

This is a division of application Ser. No. 540,720 filed October 11, 1983, U.S. Pat. No. 4,772,542; which is a division of Ser. No. 522,818 filed August 12, 1983, now U.S. Pat. No. 4,451,559; which is a continuation of Ser. No. 385,096 filed June 4, 1982 (now abandoned).

This invention relates to a silver halide photosensitive material for color photography containing a novel cyan dye image-forming coupler.

A color image is usually formed by oxidative coupling of the oxidized product, which is formed by reduction of the exposed silver halide grains with an aromatic primary amine type color developing agent, with a coupler capable of forming yellow magenta cyan dye in a silver halide emulsion.

As the coupler which may be typically employed for forming the cyan dye, there may be mentioned phenols and napthols. In particular, the basic properties required for the phenols in the light of photographic performance of the coupler are that the dye has good spectral absorption characteristics, i.e., spectrum has no absorption in green region, but sharp absorption, that the formed dye shows sufficient fastness to light, heat, moisture and the like as well as good colorability, i.e., the dye shows sufficient color sensitivity and density and further that there is no loss of the dye even if a breaching bath or breach-fix bath containing EDTA iron(III) complex as a main ingredient is exhausted owing to running.

Moreover, it has been encountered a serious problem in view of environmental pollution to remove the benzyl alcohol having incorporated into a color developing agent. However, the present situation is that a satisfactory color development can not be generally accomplished unless benzyl alcohol is added. Particularly remarkable reduction in color development can be seen with a phenol cyan coupler when benzyl alcohol is to be removed. From this point of view, there is a demand for a phenol cyan coupler with a higher color development even if benzyl alcohol is not present.

In order to meet the aforesaid requirements, there have been hitherto made various studies, but there has not yet found such a coupler capable of perfectly meeting all the foregoing properties as far as the present inventors know. For instance, as disclosed in U.S. Pat. No. 2,801,171, 6-[α-(2,4-di-tert-amylphenoxy)-butaneamido]-2,4-di-chloro-3-methylphenol shows a good fastness to light, but has a poor heat fastness, a great loss of the dye in the exhausted breach-fix bath as well as a large color reliance to benzyl alcohol and a difficult removal of benzyl alcohol from a color developing agent. U.S. Pat. No. 2,895,826 discloses 2-heptafluorobutaneamido-5-[α-(2,4-di-tert-amylphenoxy)hexaneamido]phenol, which shows excellent heat fastness and loss of dye in the exhausted breach-fix bath, but has inferior light fastness and color development. Also, the coupler as disclosed in Japanese Patent Laid-open Application No. 53-10963 encounters problems about removal of benzyl alcohol and also light fastness. Further, those phenol type cyan couplers as disclosed in U.S. Pat. No. 3,839,044, Japanese Patent Laid-open Application No. 47-37425, Japanese Patent Publication No. 48-36894, Japanese Patent Laid-open Application Nos. 50-10135, No. 50-117422, No. 50-130441, No. 50-108841, No. 50-120334 and the like are regarded as unsatisfactory with regard to heat fastness and removal of benzyl alcohol. The phenol couplers having a ureido group at the 2-position thereof as disclosed in British Patent No. 1,011,940 and U.S. Pat. Nos. 3,446,622, No. 3,966,253, No. 3,758,308, No. 3,880,661 and the like tend to form cyan dyes which shows broad spectral absorption and further considerable absorption within a green region of spectrum due to the maximum absorption in a red region or a relatively short wave range, which seems to be unfavourable in color reproduction. Other phenol couplers having a ureido group at the 2-position thereof as disclosed in Japanese Patent Laid-open Application No. 56-65134 show a considerably improved green absorption in spectral region, but still show unsatisfactory other properties.

The present inventors have made earnest studies to improve prior art noted above and, as a result, found out that the coupler as defined below can perfectly meet the above-recited characteristics required as a phenol cyan coupler.

More specifically, the silver halide photosensitive material for color photography according to the present invention is characterized by comprising a phenol type cyan coupler having the formula [I]

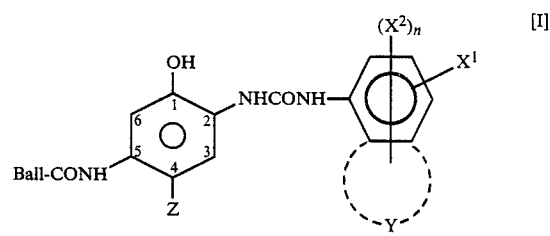

wherein
$X^1$ is —CN, —COOR$^1$, —COR$^1$, —SO$_2$OR$^1$, —SO$_2$OR$^1$,

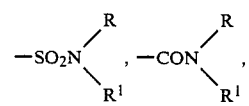

—NO$_2$ or —CF$_3$ in which R is a hydrogen atom, an alkyl group or an aryl group and R$^1$ is an alkyl group or an aryl group;
$X^2$ is a hydrogen atom, a halogen atom, a hydroxy group, a nitro group or a monovalent organic group;
Y may optionally be non-metallic atom groups capable of forming a 5- or 6-membered condensed ring;
Z is a hydrogen atom or a removable group upon coupling reaction of an oxidized product of a color developing agent;
Ball is a Ballast group; and
n is an integer of 0 to 4 inclusive; provided that when n is 2 or more, $X^2$'s may be the same or different.

As the alkyl group in the definition of R and R$^1$ of the group X, there may be usually mentioned a $C_1$ to $C_{10}$ straight or branched alkyl group, preferably $C_1$ to $C_4$ straight or branched alkyl group. As the aryl group, there may be mentioned, for example, a substituted or unsubstituted phenyl or naphthyl group.

In the above formula, the monovalent organic group represented by $X^2$ may include, for example, an alkyl group, an acyloxy group, an alkoxy group, an acyl group and the like. As the alkyl group, there may be preferably mentioned a $C_1$ to $C_5$ straight or branched alkyl group and illustrative examples thereof may include methyl, ethyl, isopropyl, butyl, tert-pentyl, chloromethyl, acetonyl, phenethyl, etc.

As the acyloxy group, there may be mentioned a $C_1$ to $C_5$ aliphatic acyloxy group and an aromatic acyloxy group and illustrative examples thereof may include acetoxy, propionyloxy, pivaloyloxy, benzoyloxy, naphthoyloxy, etc.

As the alkoxy group, there may be preferably mentioned a $C_1$ to $C_5$ aliphatic alkoxy group and an aromatic alkoxy group and illustrative examples thereof may include methoxy, tert-butoxy, ethoxymethoxy, substituted or unsubstituted phenyl.

As the acyl group, there may be preferably mentioned a $C_1$ to $C_5$ aliphatic acyl group and an aromatic acyl group and illustrative examples thereof may include acetyl, pivaloyl, acetoacetyl, benzoyl, naphthoyl, toluyl, etc.

Also, the phenyl group of the phenylureido portion in the present coupler may have a condensed ring formed together with the group Y. Where the said phenyl group has the condensed ring, the substituent $X^2$ may be located on the phenyl or the said condensed ring moiety. The condensed ring formed together with the group Y may include, for example, naphthalene, quinoline, benzothiophene, benzofuran, isocoumaran and the like.

An illustrative exaples of the group Z which may be removed in a coupling reaction, there may be mentioned, for example, a halogen atom, e.g., chlorine, bromine or fluorine atom; an aryloxy group, a carbamoyloxy group, a carbamoylmethoxy group, an acyloxy group, a sulfonamido group, a succinimido group, oxygen or nitrogen atom being attached directly to the coupling site in the said groups. Further examples thereof may include those as disclosed in U.S. Pat. No. 3,471,563, Japanese Patent Laid-open Application No. 47-37425, Japanese Patent Publication No. 48-36894, Japanese Patent Laid-open Application Nos. 50-10135, No. 50-117422, No. 50-130441, No. 51-108841, No. 50-120334, No. 52-18315, No. 53-52423, No. 53-105226 and the like.

The ballasted acylamino group (Ball) substituted at the 5-position in the phenyl moiety may act as the "ballast" which can maintain a coupler in a specific layer so as to substantially prevent the said coupler from dispersion to any other layer in a multi-layer color photographic element and should, therefore, require a sufficient "bulkiness" for such purposes. Illustravtive examples thereof may include an aromatic acylamino group and an aliphatic acylamino group. In the case of the aromatic acylamino group, the aromatic ring should have substituent(s) having a $C_5$ to $C_{18}$ alkyl chain. As the substituent having a $C_5$ to $C_{18}$ alkyl chain, there may be mentioned, for example, an alkyl group, an acyloxy group, an acylamino group, a sulfonylamino group, an alkoxycarbonyl group, a carbamoyl group, a sulfamoyl group, an alkylamino group, a dialkylamino group and the like. In the case of the aliphatic acylamino group, there may be typically mentioned those wherein the aliphatic moiety is a $C_5$ to $C_{18}$ long chain alkyl group, a phenoxyalkyl group or a phenylthioalkyl group. In the case of the phenoxyalkyl or phenylthioalkyl group, the phenoxy moiety may have a substituent having a $C_5$ to $C_{18}$ alkyl chain or the alkyl moiety may have 5 to 18 carbon atoms. As the ballasted acylamino group in the present coupler, the Ball is particularly a phenoxyalkyl group or a phenylthioalkyl group for favourable results. Illustrative examples of the acylamino group ballasted with a phenoxyalkyl group are recited below.

α-(3-Pentadecylphenoxy)butaneamido,
α-(2,4-di-tert-amylphenoxy)hexaneamido,
γ-(2,4-di-tert-amylphenoxy)butaneamido,
α-(2,4-di-tert-amylphenoxy)tetradecaneamido,
α-(4-butylsufonylaminophenoxy)tetradecaneamido,
α-(4-acetoxyphenoxy)dodecaneamido,
α-{p-[α-(4-hydroxyphenyl)-α,α-dimethyl]tolyloxy} dodecaneamido,
α-(4-carboxyphenoxy)dodecaneamido,
α-(2-chloro-4-butylsulfonylaminophenoxy)tetradecaneamido,
α-(4-dimethylaminosulfonylaminophenoxy)tetradecaneamido,
α-(3-dodecyloxyphenoxy)butaneamido,
α-(4-dodecyloxyphenoxy)butaneamido,
α-(4-hydroxyphenylthio)dodecaneamido, and
α-(4-acetylaminophenylthio)dodecaneamido.

The couplers which fall within the scope of the present invention are illustratively disclosed hereinbelow but not intended to be limited thereto.

Of the couplers which may be employed in this invention, there is preferably mentioned the coupler of the formula (I) wherein the phenylureido group substituted at the 2-position of the phenyl moiety has the following formla

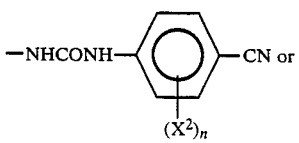

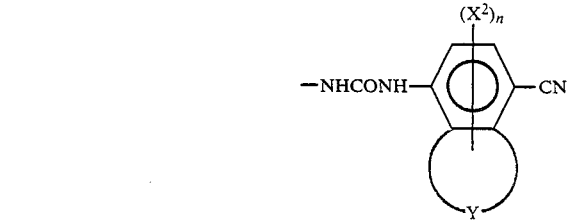

in which $X^2$, Y and n are as defined above.

Another preferable coupler of the present invention has the formula [II]

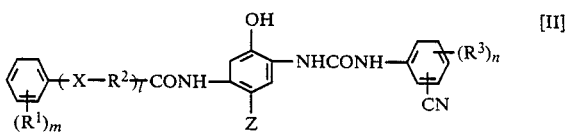

wherein X is an oxygen atom or a sulfur atom; $R^2$ is a $C_1$ to $C_{20}$ straight or branched alkylene group; the —CN group is located at the 2- or 3-position in the phenyl moiety to the ureido group; $R^3$ is a hydrogen atom, a halogen atom (particularly preferably, fluorine or bromine) or a monovalent organic group such as an alkyl group (preferably, a $C_1$-$C_4$ straight or branched alkyl group, particularly preferably methyl-tert-butyl), an aryl group (preferably, an unsubstituted or substituted phenyl group), a heterocyclic group (preferably, an N-containing heterocyclic group, particularly preferably pyrrolidine, piperidine), a hydroxy group, an alkoxy group (preferably, a $C_1$ to $C_8$ unsubstituted or substituted alkoxy group, particularly preferably methoxy, tert-butyloxy, methoxycarbonylmethoxy), an aryloxy group (preferably, an unsubstituted or substituted phenoxy group), an acyloxy group (preferably, an unsubstituted or substituted alkylcarbonyloxy group or an arylcarbonyloxy group), a mercapto group, an alkylthio group (preferably, a $C_1$ to $C_8$ unsubstituted or substituted alkylthio group, particularly preferably a methylthio group), a nitro group, an acyl group (preferably, a $C_1$ to $C_8$ alkylcarbonyl group, particularly preferably an acetyl group or a pivaloyl group), an amino group, an alkylamino group (preferably, a $C_1$ to $C_4$ straight or branched alkylamino group, particularly preferably a methylamino group, an ethylamino group, a tert-butylamino group), a dialkylamino group (preferably, a dimethylamino group or a diethylamino group); $R^1$ is a group optionally selected from a hydrogen atom, a halogen atom (preferably, chlorine or bromine), an alkyl group (preferably, a $C_1$ to $C_{20}$ straight or branched alkyl group, preferably methyl, tert-butyl, tert-pentyl, tert-octyl, dodecyl, pentadecyl), an aryl group (preferably, phenyl), a heterocyclic group (preferably, an N-containing heterocyclic group), an aralkyl group (preferably, benzyl, phenethyl), an alkoxy group (preferably, a $C_1$ to $C_{20}$ straight or branched alkyloxy group, particularly preferably methoxy, ethoxy, tert-butoxy, octyloxy, decyloxy, dodecyloxy), an aryloxy group (preferably, phenoxy), a hydroxy group, an acyloxy group (preferably, an unsubstituted or substituted alkylcarbonyloxy group, an arylcarbonyloxy group, particularly preferably acetoxy, benzoyloxy), a carboxyl group, an alkoxycarbonyl group (preferably, a $C_1$ to $C_{20}$ straight or branched alkyloxycarbonyl group), an aryloxycarbonyl group (preferably, an unsubstituted or substituted phenoxycarbonyl group), a mercapto group, an alkylthio group (preferably, a $C_1$ to $C_{20}$ straight or branched, unsubstituted or substituted alkylthio group), an arylthio group (preferably, an unsubstituted or substituted phenylthio group), an alkylsulfonyl group (preferably, a $C_1$ to $C_{20}$ straight or branched alkylsulfonyl group), an acyl group (preferably, a $C_1$ to $C_{20}$ straight or branched alkylcarbonyl group, an unsubstituted or substituted benzenecarbonyl group), an acylamino group (preferably, a $C_1$ to $C_{20}$ straight or branched alkylcarboamido group or an unsubstituted or substituted benzenecarboamido group), a sulfonamido group (preferably, a $C_1$ to $C_{20}$ straight or branched, unsubstituted or substituted alkylsulfonamido group or an unsubstituted or substituted benzenesulfonamido group), a carbamoyl group (preferably, a $C_1$ to $C_{20}$ straight or branched alkylaminocarbonyl group or an unsubstituted or substituted phenylaminocarbonyl group and a sulfamoyl group (preferably, a $C_1$ to $C_{30}$ straight or branched alkylaminosulfonyl group or an unsubstituted or substituted phenylaminosulfonyl group); n is an integer of 0–3; m is an integer of 1 to 4; and l is an integer of 0 or 1; and Z is as defined in the above formula [I].

Still another preferred cyan couplers in the present invention has the formula [III]

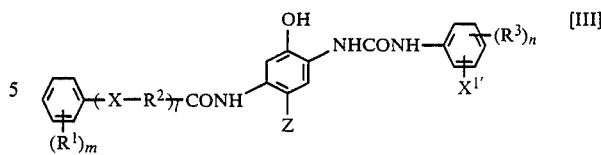

In the above formula, X is an oxygen atom or a sulfur atom; $R^2$ is a straight or branched alkylene group having 1 to 20 carbon atoms; $X^{1'}$ is $-COOR^1$, $-SO_2R^1$, $-NO_2$, $-COR^1$,

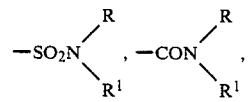

$-SO_2OR^1$ or $-CF_3$ in which R is a hydrogen atom, an alkyl group (preferably, a $C_1$ to $C_4$ straight or branched alkyl group) or an aryl group (preferably, an unsubstituted or substituted phenyl group); $R^1$ is an alkyl group (preferably, a $C_1$ to $C_4$ straight or branched alkyl group) or an aryl group (preferably, an unsubstituted or substituted phenyl group) and R and $R^1$ together may form a 5- or 6-membered ring; and $R^3$ is a hydrogen atom, a halogen atom or a monovalent organic group such as an alkyl group (preferably, a $C_1$ to $C_4$ straight or branched alkyl group, particularly preferably, methyl, tert-butyl), an aryl group (preferably, an unsubstituted or substituted phenyl group), a heterocyclic group (preferably, an N-containing heterocyclic group, particularly preferably pyrrolidine or piperidine), a hydroxy group, an alkoxy group (preferably, a $C_1$ to $C_8$ unsubstituted or substituted alkoxy group, particularly preferably methoxy, tert-butoxy, methoxycarbonylmethoxy), an aryloxy group (preferably, an unsubstituted or substituted phenoxy group), an acyloxy group (preferably, an unsubstituted or substituted alkylcarbonyloxy group or an arylcarbonyloxy group), a mercapto group, an alkylthio group (preferably, a $C_1$ to $C_8$ unsubstituted or substituted alkylthio group, particularly preferably a methylthio group), a nitro group, an acyl group (preferably, a $C_1$ to $C_8$ alkylcarbonyl group, particularly preferably an acetyl group or a pivaloyl group), an amino group, an alkylamino group (preferably, a $C_1$ to $C_4$ straight or branched alkylamino group, particularly preferably a methylamino group, an ethylamino group or a tert-butylamino group) or a dialkylamino group (preferably, a dimethylamino group or a diethylamino group); $R^1$ is a hydrogen atom, a halogen atom (preferably, chlorine or bromine), an alkyl group (preferably, a $C_1$ to $C_{20}$ straight or branched alkyl group, particularly preferably methyl, tert-butyl, tert-pentyl, tert-octyl, dodecyl or pentadecyl), an aryl group (preferably, phenyl), a heterocyclic group (preferably, an N-containing heterocyclic group), an aralkyl group (preferably, benzyl or phenethyl), an alkoxy group (preferably, a $C_1$ to $C_{20}$ straight or branched alkoxy group, particularly preferably methoxy, ethoxy, tert-butoxy, octyloxy, decyloxy, dodecyloxy), an aryloxy group (preferably, phenoxy), a hydroxy group, an acyloxy group (preferably, an unsubstituted or substituted alkylcarbonyloxy group or an arylcarbonyloxy group, particularly preferably acetoxy or benzoyloxy), a carboxy group, an alkoxycarbonyl group (preferably, a $C_1$ to $C_{20}$ straight or branched, unsubstituted or substituted alkyloxycarbonyl group), an aryloxycarbonyl group (preferably, an unsubstituted or substituted phenoxycarbonyl group), a mercapto group, an alkylthio group (preferably, a $C_1$ to $C_{20}$ straight or branched, unsubstituted or substituted alkylthio group), an arylthio group (preferably, an unsubstituted or substituted phenylthio group), an alkylsulfonyl group (preferably, a $C_1$–$C_{20}$ straight or branched alkylsulfonyl group), an arylsulfonyl group (preferably, an unsubstituted or substituted benzenesulfonyl group), an acyl group (preferably, a $C_1$ to $C_{20}$ straight or branched alkylcarbonyl group or an unsubstituted or substituted benzenesulfonyl group), an acylamino group (preferably, a $C_1$ to $C_{20}$ straight or branched alkylcarboamido group or an unsubstituted or substituted benzenecarboamido group), a sulfonamido group (preferably, a $C_1$ to $C_{20}$ straight or branched, unsubstituted or substituted alkylsulfonamido group or an unsubstituted or substituted benzenesulfonamido group), a carbamoyl group (preferably, a $C_1$ to $C_{20}$ straight or branched alkylaminocarbonyl group or an unsubstituted or substituted phenylaminocarbonyl group) or a sulfamoyl group (preferably, a $C_1$ to $C_{20}$ straight or branched alkylaminosulfonyl group or an unsubstituted or substituted phenylaminosulfonyl group); and Z is as defined in the above formula [I]. In the formula III, n is 0 to 3; m is 1 to 4; l is 0 or 1; and $R^2$ is a straight or branched alkylene group.

Illustrative examples of the coupler, which may be employed in the photosensitive material for color photography according to this invention, are given hereinbelow.

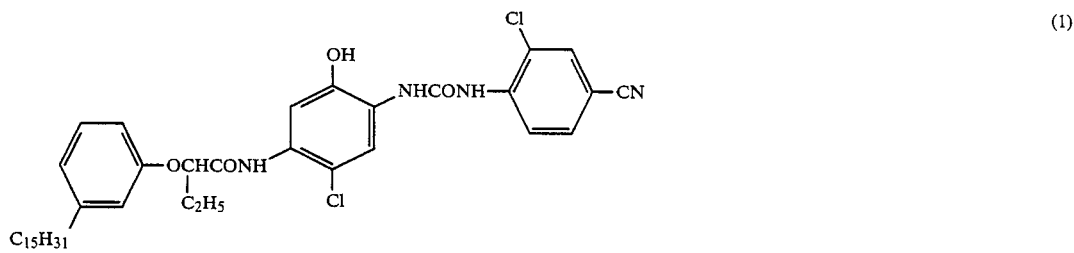

(1)

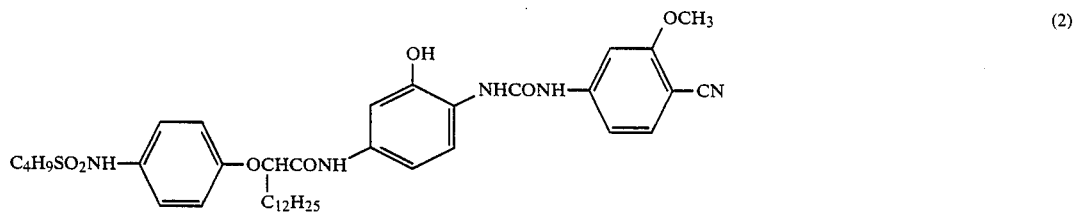

(2)

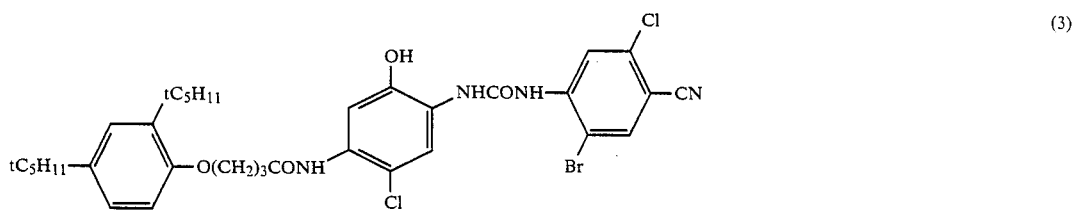

(3)

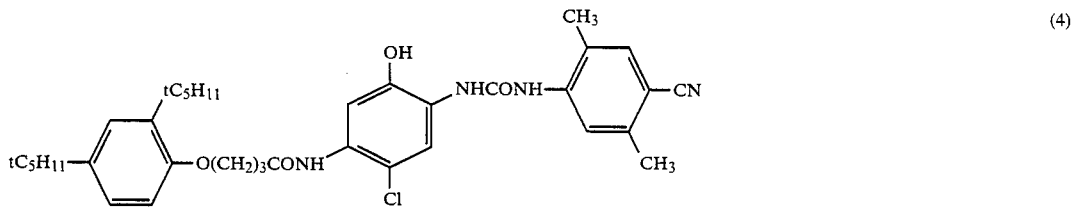

(4)

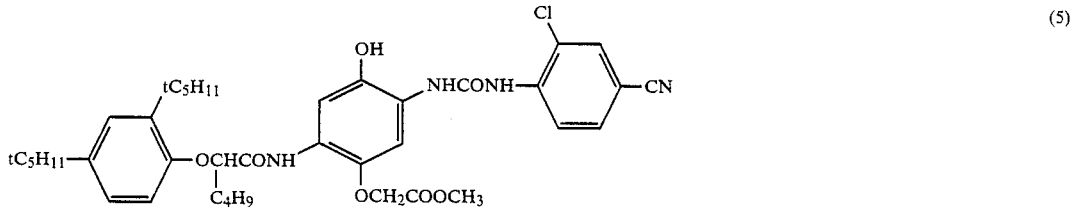

(5)

-continued
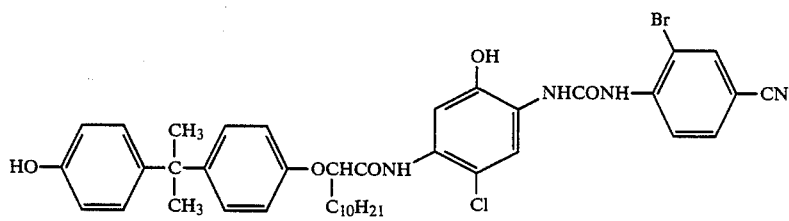 (6)
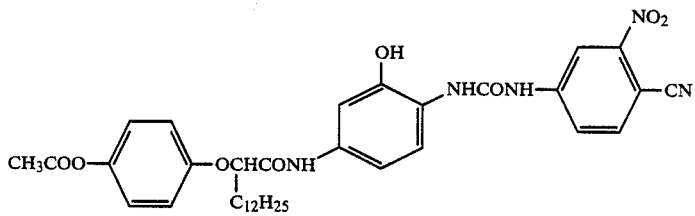 (7)
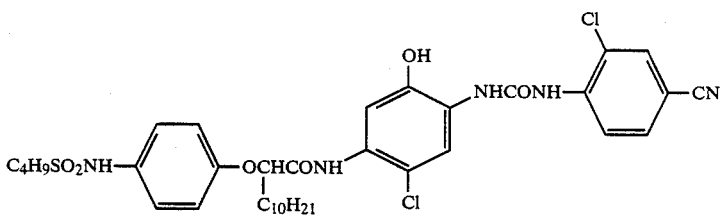 (8)
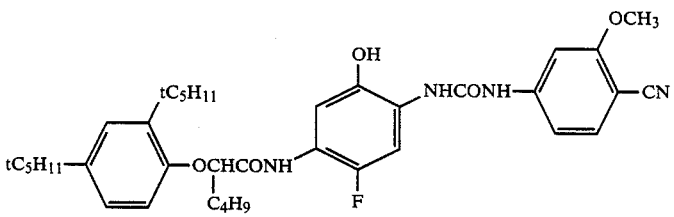 (9)
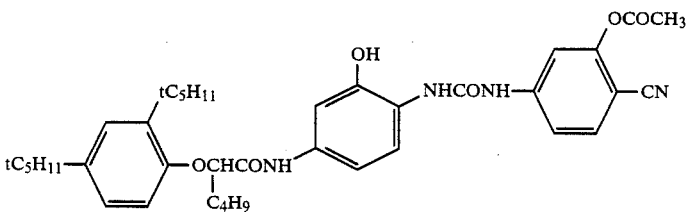 (10)
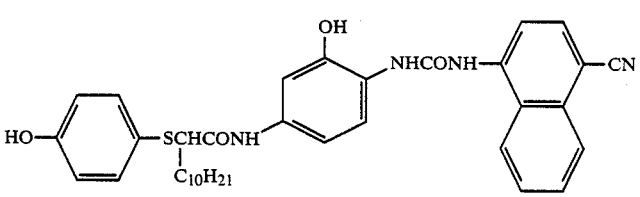 (11)
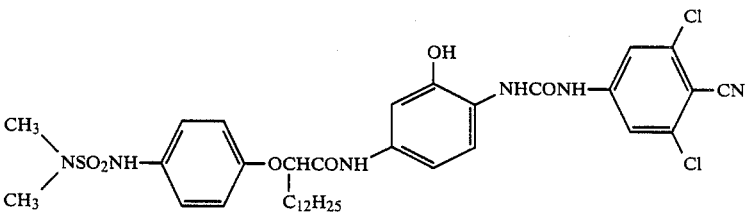 (12)

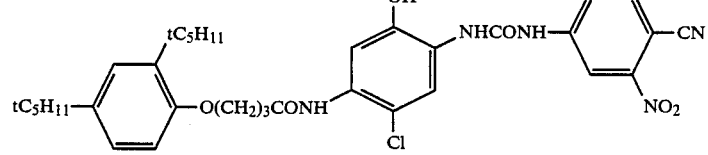
(13)
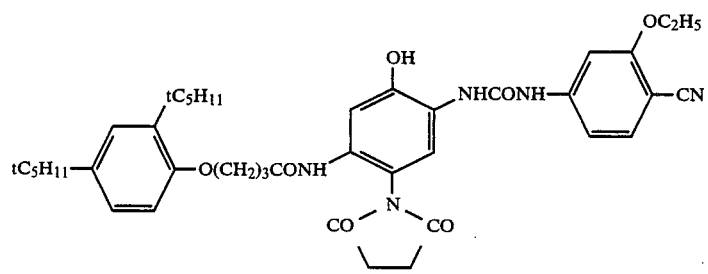
(14)
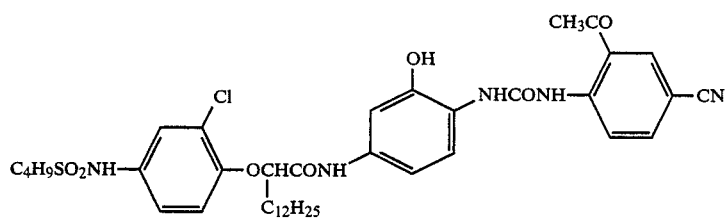
(15)
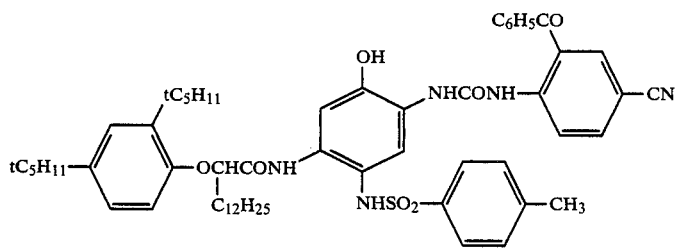
(16)
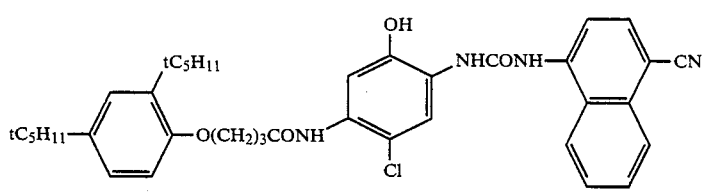
(17)
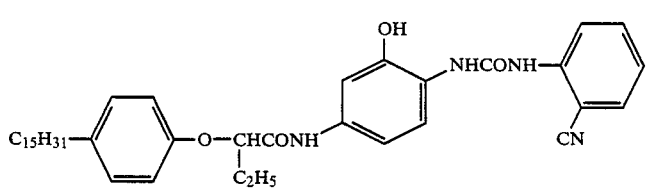
(18)
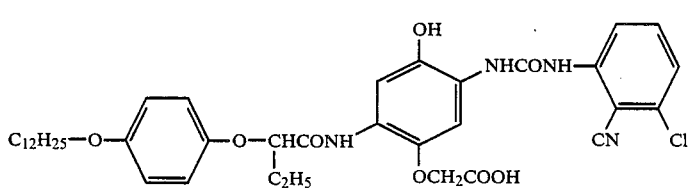
(19)

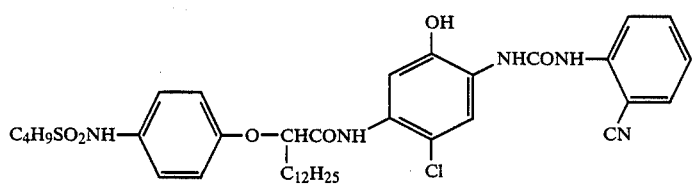
(20)
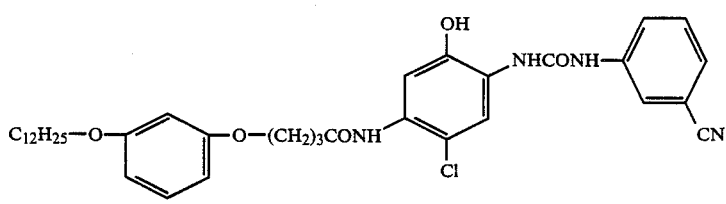
(21)
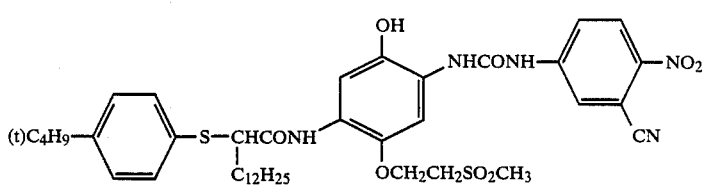
(22)
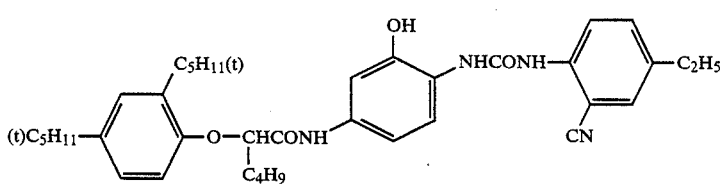
(23)
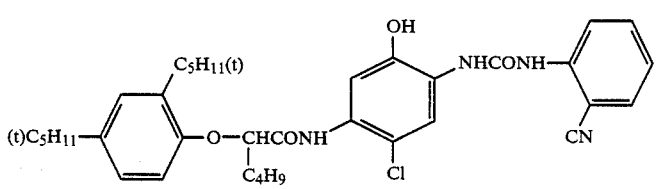
(24)
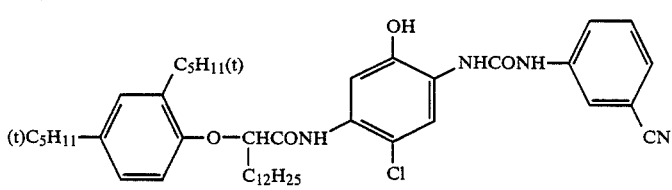
(25)
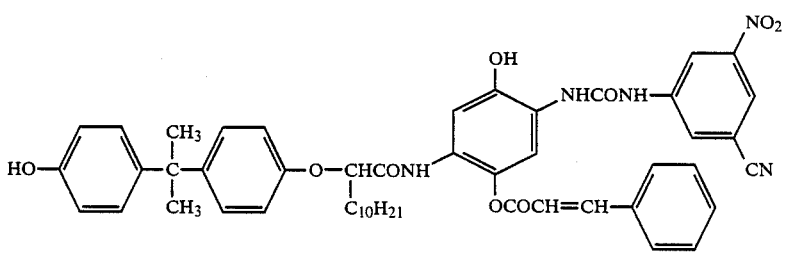
(26)

-continued

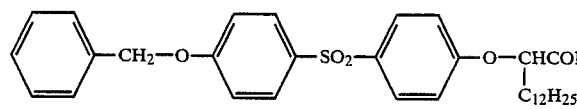
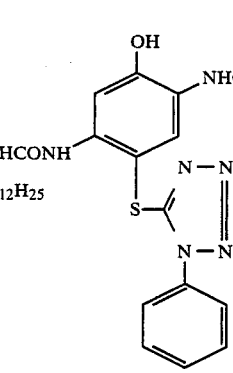

(27)

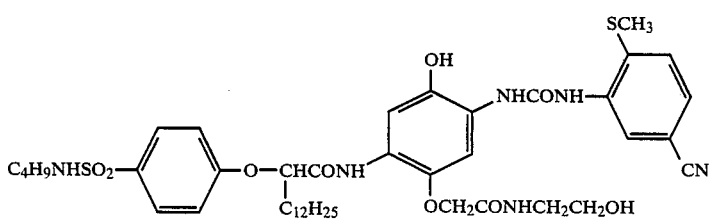

(28)

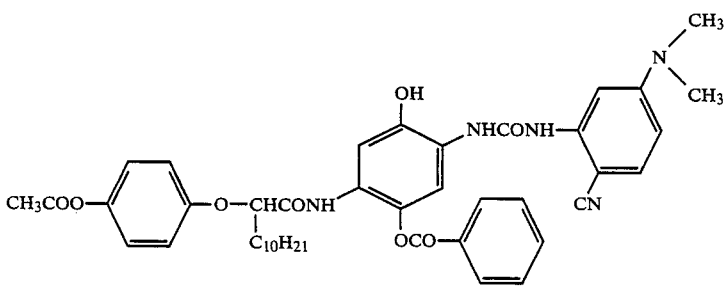

(29)

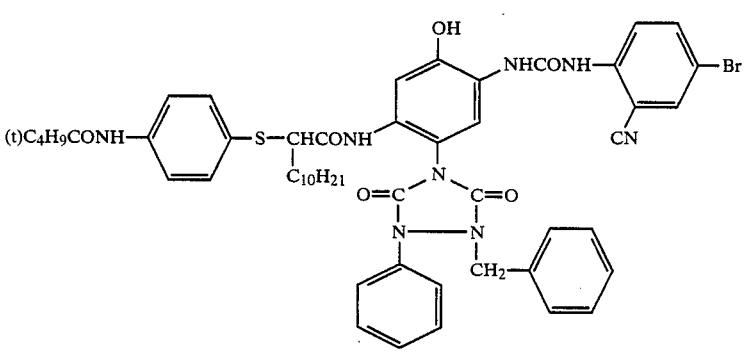

(30)

The coupler which may be employed in this invention can be prepared by reacting a substituted p-cyanophenyl isocyanate with a suitable aminophenol, for example, 2-amino-5-nitrophenol or 2-amino-4-chloro-5-nitrophenol to produce a 2-(substituted p-cyanophenyl)ureido compound. Then, the nitro group of the latter compound is reduced to the amino group in a conventional manner and the ballast group is attached to the acid amino group to produce the desired coupler.

Representative synthesis examples of the present coupler are given below for illustrating purpose only.

SYNTHESIS EXAMPLE 1

Coupler No. 1

(A) Synthesis of 2-(p-cyano-m-methoxyphenyl)ureido-5-nitrophenol

A suspension of 15.4 g. of 2-amino-5-nitrophenol in 300 ml. of toluene was refluxed. A solution of 17.4 g. of p-cyano-m-methoxyphenyl isocyanate in 150 ml. of toluene was added dropwise thereto. After completion of the dropwise addition, the resulting mixture was heated under reflux for 1 hour and then cooled. The precipitate was filtered and washed successively with hot toluene and alcohol to give 22 g. of the end product.

(B) Synthesis of Coupler No. 2

The nitrophenol produced in (A) (6.6 g.) was subjected to hydrogenation at ordinary temperature and atmospheric pressure in 200 ml. of alcohol using palladium-carbon catalyst. After the catalyst was filtered off, the filtrate was concentrated and the residue was dissolved in 200 ml. of acetonitrile. To the resulting solution were added 1.6 g. of pyridine and then 9.5 g. of 2-(4-butylsulfonylaminophenoxy)tetradecanoyl chloride under stirring at room temperature. After stirring was continued at room temperature for 5 hours, the reaction mixture was poured into water, extracted with ethyl acetate. The ethyl acetate was distilled off and the residue crystallized from methanol and then acetonitrile to give 7.2 g. of the end product, which was identified by mass spectrum and NMR spectrum.

SYNTHESIS EXAMPLE 2

Coupler No. 1

(A) Synthesis of 2-(o-chloro-p-cyanophenyl)ureido-4-chloro-5-nitrophenol

A mixture of 18.8 g. of 2-amino-4-chloro-5-nitrophenol, 27.3 g. of phenyl o-chloro-p-cyanophenylcarbamate and 0.6 g. of imidazole in 400 ml. of xylene was heated under reflux for 5 hours. After cooling, the precipitate was filtered off and the residue was washed with xylene and then alcohol to give 23.5 g. of the end product.

(B) Synthesis of Coupler No. 1

The nitrophenol produced in (A) (11 g.) was subjected to hydrogenation at ordinary temperature and atmospheric pressure in 300 ml. of alcohol using palladium-carbon catalyst. After completion of the reaction, the catalyst was filtered off, the filtrate was concentrated and to the residue were added 250 ml. of acetonitrile. To the resulting mixture were added 2.4 g. of pyridine and then 12.3 g. of 2-(3-pentadecylphenol)butanoyl chloride under stirring at room temperature. After stirring at room temperature for 6 hours, the reaction mixture was poured into water and extracted with ethyl acetate. The ethyl acetate was distilled off and the residue was chromatographed over silica gel using as eluant benzene-ethyl acetate. The fractions containing the end product were combined and the solvent was distilled off. The residue was recrystallized from methanol to give 5.8 g. of the end product, which was identified by mass spectrum and NMR spectrum.

SYNTHESIS EXAMPLE 3

Coupler No. 24

Synthesis of 2-(o-cyanophenyl)ureido-4-chloro-5-{α-(2,4-di-tert-pentylphenoxy)hexaneamido}phenol To a suspension of 18.9 g. of 2-amino-4-chloro-5-nitrophenol in 200 ml. of toluene was added a solution of 16 g. of o-cyanophenyl isocyanate in 100 ml. of toluene under stirring at room temperature. The resulting mixture was boiled under reflux for 1 hour and then allowed to cool to room temperature. The crystalline substance thus separated was filtered, washed with hot toluene and then cold methanol to give 31 g. of the product with mp 251°-255° C.

A suspension of 3.3 g. of the so obtained 2-(o-cyanophenyl)ureido-4-chloro-5-nitrophenol in 200 ml. of tetrahydrofuran was subjected to catalytic reduction using palladium-carbon catalyst. After a theoretical volume of hydrogen was absorbed, 0.9 ml. of pyridine was added to the reaction mixture and then a solution of 3.7 g. of 2-(2,4-di-tert-pentylphenoxy)hexanoyl chloride in 50 ml. of tetrahydrofuran was added thereto under stirring at room temperature. After completion of the addition, the reaction was continued for further 1 hour and the catalyst was filtered off. The filtrate was added to ice-water containing 10 ml. of conc. hydrochloric acid and extracted with ethyl acetate. The extract was washed with water, dried over sodium sulfate and concentrated under reduced pressure to leave an oily substance. The substance was solidified with a mixture of benzene with hexane to give 2.6 g. of the end product as a white solid with mp 163°-168° C.

| Analysis (%) | C | H | N | Cl |
|---|---|---|---|---|
| Calc'd: | 68.28 | 7.16 | 8.85 | 5.60 |
| Found: | 67.95 | 6.88 | 9.03 | 5.82 |

SYNTHESIS EXAMPLE 4

Coupler No. 25

Synthesis of 2-(m-cyanophenyl)ureido-4-chloro-5-{α-(2,4-di-tert-pentylphenoxy)tetradecaneamido}phenol To a suspension of 18.9 g. of 2-amino-4-chloro-5-nitrophenol in 200 ml. of toluene was added a solution of 16 g. of m-cyanophenyl isocyanate in 100 ml. of toluene under stirring at room temperature. The resulting mixture was boiled under reflux for 1 hour. Thereafter, the reaction mixture was allowed to cool to room temperature. The crystalline substance thus separated was filtered, washed with hot toluene and then cold methanol and dried over sodium sulfate to give 33 g. of the product with mp 255°-259° C.

A suspension of 3.3 g. of the so obtained 2-(m-cyanophenyl)ureido-4-chloro-5-nitrophenol in 200 ml. of tetrahydrofuran was subjected to catalytic reduction using palladium-carbon catalyst. After a theoretical volume of hydrogen was absorbed, 0.9 ml. of pyridine was added to the reaction mixture and a solution of 4.8 g. of 2-(2,4-di-tert-pentylphenoxy)tetradecanoyl chloride in 50 ml. of tetrahydrofuran was added thereto under stirring at room temperature. After completion of the addition, the reaction was continued for further 1 hour. The catalyst was filtered off, the filtrate was added to ice-water containing 10 ml. of conc. hydrochloric acid and extracted with ethyl acetate. The extract was washed with water, dried over sodium sulfate and concentrated under reduced pressure to leave an oily substance. The substance was purified by silica gel column chromatography and solidified with hexane to give 2.7 g. of the end product as a white solid with mp 185°-188° C.

| Analysis (%) | C | H | N | Cl |
|---|---|---|---|---|
| Calc'd: | 70.89 | 8.25 | 7.52 | 4.76 |
| Found: | 69.91 | 7.86 | 7.72 | 5.02 |

SYNTHESIS EXAMPLE 5

Coupler No. 45

Synthesis of
2-(3-ethoxycarbonylphenyl)ureido-4-chloro-5-{α-(4-butylsulfonylamidophenoxy)tetradecaneamido}phenol To a suspension of 18.9 g. of 2-amino-4-chloro-5-nitrophenol in 200 ml. of toluene was added a solution of 21 g. of 3-ethoxycarbonylphenyl isocyanate in 100 ml. of toluene under stirring at room temperature. The resulting mixture was boiled under reflux for 1 hour and then allowed to cool to room temperature. The crystalline substance thus separated was filtered, washed with methanol and then dried to give 34 g. of the product as a pale yellow crystal with mp 261°–266° C.

A mixture of 19 g. of 2-(3-ethoxycarbonylphenyl)ureido-4-chloro-5-nitrophenol in 600 ml. of alcohol was subjected to catalytic reduction using palladium carbon catalyst. After a theoretical volume of hydrogen was absorbed, the catalyst was filtered off and the filtrate was concentrated under reduced pressure to give 17 g. of the crude product.

To a homogeneous solution of 3.5 g. of the so obtained 2-(3-ehtoxycarbonylphenyl)ureido-4-chloro-5-aminophenol in a mixture of 100 ml. of acetonitrile and 0.9 ml. of pyridine was added a solution of 4.7 g. of α-(4-butylsulfonylamidophenoxy)tetradecanoyl chloride in 50 ml. of acetonitrile under stirring at room temperature. After completion of the addition, the reaction was continued for further 1 hour, the reaction mixture was added to ice-water, extracted with ethyl acetate, the extract was washed with water, dried over sodium sulfate and concentrated under reduced pressure. The residue was purified by silica gel column chromatography and solidified with hexane to give 3.7 g. of the end product as a white solid with mp 146°–149° C.

| Analysis (%) | C | H | N | Cl | S |
|---|---|---|---|---|---|
| Calc'd: | 61.01 | 7.04 | 7.12 | 4.50 | 4.07 |
| Found: | 59.89 | 7.12 | 7.09 | 4.63 | 3.85 |

SYNTHESIS EXAMPLE 6

Coupler No. 50

Synthesis of
2-(3-trifluoromethyl)phenylureido-4-chloro-5-{α-(2,4-di-tert-pentylphenoxy)hexaneamido}phenol To a suspension of 8.9 g. of 2-amino-4-chloro-5-nitrophenol in 200 ml. of toluene were added 20.6 g. of 3-trifluoromethylphenyl isocyanate under stirring at room temperature. The reaction mixture was boiled under reflux for 3 hours and thereafter allowed to cool to room temperature. The crystalline substance thus separated was filtered, washed with methanol and dried to give 36 g. of a pale yellow solid.

A mixture of 18.8 g. of the so obtained 2-(3-trifluoromethyl)phenylureido-4-chloro-5-nitrophenol in 600 ml. of ethanol was subjected to catalytic reduction using palladium-carbon catalyst. After a theoretical volume of hydrogen was absorbed, the catalyst was removed by filtration while hot. The filtrate was concentrated under reduced pressure to give 16 g. of crude crystalline substance.

To a mixture of 3.5 g. of the so obtained 2-(3-trifluoromethyl)phenylureido-4-chloro-5-aminophenol in a mixture of 100 ml. of acetonitrile with 0.9 ml. of pyridine was added a solution of 3.7 g. of α-(2,4-di-tert-pentylphenoxy)hexanoyl chloride in 50 ml. of acetonitrile under stirring at room temperature. After completion of the addition, the reaction was continued for further 1 hour, added to ice-water and extracted with ethyl acetate. The extract was washed with water, dried over sodium sulfate and then concentrated under reduced pressure to leave an oily substance. The crude substance thus obtained was purified by silica gel column chromatography and solidified with hexane to give 3.6 g. of a white solid with mp 151°–156° C.

| Analysis (%) | C | H | N | Cl | F |
|---|---|---|---|---|---|
| Calc'd: | 63.94 | 6.71 | 6.22 | 5.24 | 8.23 |
| Found: | 64.11 | 6.68 | 6.19 | 5.15 | 8.34 |

The cyan dye-forming coupler, which may be employed in this invention, can be similarly used according to the methods and techniques commonly employed for conventional cyan dye-forming couplers. Typically the coupler can be blended with a silver halide emulsion and the emulsion is coated onto a base to form a photographic element.

The photographic element may be monochromatic or multicolor one. In the case of a multicolor photographic element, the present cyan dye-forming coupler may be usually incorporated into a red sensitive emulsion, but contain a non-sensitized emulsion or dye-image forming constituent units having photosensitivity to respective three primary colors in spectrum. Each constituent unit may comprise a monoemulsion layer or a multi-emulsion layer which has a photosensitivity to a certain region in spectrum. Element layers including the image-forming constituent unit layer may be arranged in any optional order as is well-known to those skilled in the art. Typical multi-color photographic element comprises a cyan dye-forming image-forming constituent unit, said unit comprising at least one red sensitive silver halide emulsion layer containing at least one cyan dye-forming coupler (at least one of the coupler is the present coupler) and a yellow dye image-forming constituent unit, said unit comprising at least one blue sensitive silver halide emulsion layer containing at least one magenta dye-forming coupler, both units being carried on a base. The element may further contain additional layers, for example, a filter layer, an interlayer, a protective layer, a subbing layer and the like.

The present coupler may be incorporated into an emulsion according to any well-known techniques. For instance, the present coupler alone or in combination with other ingredients may be dissolved in a high boiling organic solvent with a boiling point of 175° C. or higher such as tricresyl phosphate, dibutyl phthalate and the like or a low boiling organic solvent such as butyl acetate, butyl propionate and the like alone or, if necessary, in combination therewith, the resulting solution is admixed with an aqueous solution of gelatin containing a surface active agent, the resulting mixture is then emulsified by a high speed rotary mixer or a colloid mixer and incorporated into a silver halide to prepare a silver halide emulsion which may be employed in this invention. And, where the present coupler is to be incorporated into the present silver halide emulsion, the coupler is employed in a range of usually about 0.07–0.7 mole, preferably 0.1–0.4 mole, per mole of the silver halide.

As the silver halide which may be employed in the present silver halide emulsion, there may be included any optional silver halides commonly employed for a silver halide emulsion such as silver bromide, silver chloride, silver iodobromide, silver chlorobromide, silver chloroiodobromide and the like.

A silver halide emulsion which constitutes the present silver halide emulsion may be prepared by any various conventional methods such as the method disclosed, for example, in Japanese Patent Publication No. 46-7772: Namely, a method for preparing the so called conversion emulsion wherein a silver salt grain emulsion is formed, the said grain comprising at least partly a silver salt having a higher solubility than that of silver bromide, and then at least part of the said silver salt is converted to silver bromide or silver iodobromide or a method for preparing the so called Lippmann emulsion comprising silver halide fine grains having an average grain size of not more than 0.1μ.

Moreover, the present silver halide emulsion may be chemically sensitized with a sulfur sensitizer such as allylthiocarbamide, thiourea, cystine and the like, an active or inactive selenium sensitizer, a reduction sensitizer such as a stannous salt, a polyamine and the like, a noble metal sensitizer such as a gold sensitizer, typically potassium aurithiocyanate, potassium chloroaurate, 2-aurosulfobenzothiazole methyl chloride and the like, or a water-soluble rutenium, rhodium, iridium or like salt sensitizer, typically ammonium chloropalladate, potassium chloroplatinate, sodium chloropalladate and the like alone or in any combination therewith.

The present silver halide emulsion may also contain a wide variety of well-known photographic additives, for example, those disclosed in "Research Disclosure", 1978, December, item 17643.

The present silver halide emulsion may have spectral sensitization upon selection of any suitable sensitizing dyes in order to afford a photosensitivity to the sensitive wave length region required for a red sensitive emulsion. As the spectrally sensitizing dye, there may be employed one or more of various dyes and, for this invention, there may be mentioned, for example, those cyanine dyes, merocyanine dyes or complex cyanine dyes as disclosed in U.S. Pat. Nos. 2,269,234, 2,270,378, 2,442,710, 2,454,629, 2,776,280.

The color developing solution which may be employed in this invention may preferably contain as a main ingredient an aromatic primary amine type color developing agent. Illustrative examples of such color developing agent may be typically of a p-phenylenediamine type; for example, diethyl-p-phenylenediamine hydrochloride, monomethyl-p-phenylenediamine hydrochloride, dimethyl-p-phenylenediamine hydrochloride, 2-amino-5-diethylaminotoluene hydrochloride, 2-amino-5-(N-ethyl-N-dodecylamino)toluene, 2-amino-5-(N-ethyl-N-β-methanesulfonamidoethyl)aminotoluene sulfate, 4-(N-ethyl-N-β-methanesulfonamidoethylamino)aniline, 2-amino-5-(N-ethyl-N-β-methoxyethyl)aminotoluene, 4-(N-ethyl-N-β-hydroxyethylamino)aniline and the like.

After development, conventional steps of bleaching for removal of silver or a silver halide, fixing or bleach-fixing, washing and drying may be applied.

The following examples are given for illustrating this invention more concretely, but it should be noted that embodiments of this invention be not limited thereto.

EXAMPLE 1

Each 0.03 mole of the present couplers indicated in the following Table 1 and the following control couplers A, B and C was added to a mixture of the same weight of dibutyl phthalate and 3 times volume of ethyl acetate and the mixture was heated to 60° C. to form a complete solution. The solution was added to an aqueous solution of "Alkanol B" (alkylnaphthalene sulfonate, manufactured by E. I. DuPont) and gelatin, the resulting mixture was emulsified by a colloid mill to prepare each coupler dispersion. Then, the coupler dispersion was added to a silver chlorobromide emulsion (20 mole % silver bromide; containing 0.1 mole silver) and the mixture was coated onto a polyethylene laminated paper and then dried to prepare 6 silver halide photosensitive materials for color photography having a stable coated film (Samples No. 1 to No. 6).

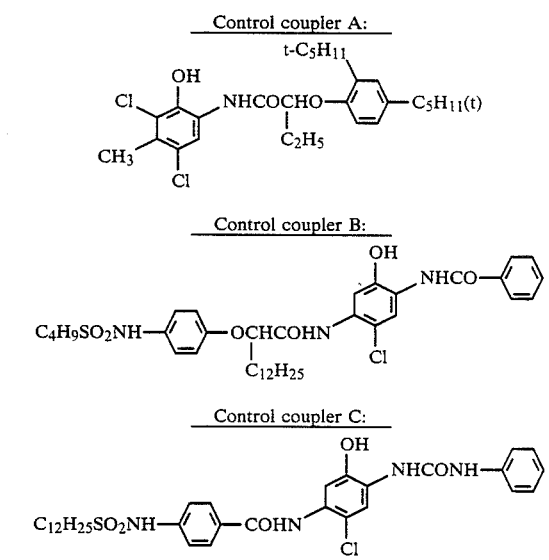

The sample was subjected to wedge exposure according to a conventional method and then treated as stated hereunder. However, the color developing step was effected with two sorts of color developing compositions, namely color development (1) with benzyl alcohol and color development (2) without benzyl alcohol.

| (Treatment) Treatment step (30° C.) | Treatment time |
| --- | --- |
| Color development | 3 min. 30 sec. |
| Bleach-fixing | 1 min. 30 sec. |
| Water washing | 2 min. |

Formulations for each step are given below.

| (Color developing solution, composition 1) | |
| --- | --- |
| 4-Amino-3-methyl-N-ethyl-N-(β-methanesulfonamidoethyl)-aniline sulfate | 5.0 g. |
| Benzyl alcohol | 15.0 ml. |
| Sodium hexametaphosphate | 2.5 g. |
| Anhydrous sodium sulfite | 1.85 g. |
| Sodium bromide | 1.4 g. |
| Potassium bromide | 0.5 g. |
| Borax | 39.1 g. |
| Water to make up 1 l. | |

| | -continued | |
|---|---|---|
| Adjusted to pH 10.30 with NaOH | | |
| (Color developing solution, composition 2) | | |
| The same formulation as in the above composition 1 except that the benzyl alcohol was omitted. | | |
| (Bleach-fixing solution composition) | | |
| Ethylenediaminetetraacetate iron ammonium complex | 50 g. | |
| Ammonium sulfite (40% aqueous solution) | 50 ml. | |
| Ammonium thiosulfate (70% aqueous solution) | 140 ml. | |
| Aqueous ammonia (28% solution) | 20 ml. | |
| Ethylenediaminetetraacetic acid | 4 g. | |
| Water to make up 1 l. | | |

Each sample was determined for its photographic characteristics. The results are summarized in Table 1, wherein relative sensitivity values are represented in terms of the maximum sensitivity value when treated with the color developing solution 1 as 100.

TABLE 1

| | | Color development 1 | | Color development 2 | |
|---|---|---|---|---|---|
| Sample No. | Coupler applied | Relative sensitivity | Maximum density | Relative sensitivity | Maximum density |
| 1 | No. 6 | 98 | 2.22 | 70 | 1.77 |
| 2 | No. 8 | 100 | 2.24 | 75 | 1.80 |
| 3 | No. 17 | 98 | 2.20 | 71 | 1.80 |
| 4 | Control coupler A | 97 | 2.17 | 50 | 1.39 |
| 5 | Control coupler B | 94 | 1.90 | 61 | 1.45 |
| 6 | Control coupler C | 86 | 1.81 | 55 | 1.52 |

As can be seen from the above Table 1, the samples prepared from the present couplers show a good sensitivity and the maximum density and thus are excellent, irrespective of the presence or absecne of benzyl alcohol.

Further, determination of color spectrum has revealed that the dye with the present coupler show the absorption maximum within a relatively longer wave length range of a red region and little absorption within a short wave length range and thus show an excellent color purity.

EXAMPLE 2

The samples as prepared in the same manner as in the above Example 1 were tested for light fastness, heat fastness and moisture fastness of their dye images. The results are summarized in Table 2.

TABLE 2

| | | Color development 1 | | | Color development 2 | | |
|---|---|---|---|---|---|---|---|
| Sample No. | Coupler applied | Light fastness | Heat fastness | Moisture fastness | Light fastness | Heat fastness | Moisture fastness |
| 7 | No. 6 | 90 | 98 | 96 | 91 | 97 | 95 |
| 8 | No. 8 | 88 | 96 | 97 | 87 | 96 | 96 |
| 9 | No. 17 | 85 | 97 | 96 | 84 | 96 | 96 |
| 10 | Control coupler A | 85 | 40 | 62 | 85 | 42 | 60 |
| 11 | Control coupler B | 65 | 90 | 91 | 55 | 95 | 90 |
| 12 | Control coupler C | 55 | 91 | 90 | 51 | 90 | 90 |

In the above Table 2, light fastness is represented in terms of the remaining density of each image after exposure to a xenon fadeometer over 300 hours by the use of the density before exposure as 100; moisture fastness is represented in terms of the remaining density after storage under a relative mositure of 70% over 3 weeks by the use of the density before testing as 100; and heat fastness is represented in terms of the remaining density after storage at 77° C. over 3 weeks by the use of the density before testing as 100, provided that initial density is 1.0.

As is apparent from the above Table 2, the control coupler A is excellent in light fastness, but not so good in heat and moisture fastness, while control couplers B and C are excellent in heat and moisture fastness but not so good in light fastness upon color development 2. To the contrary, the present couplers Nos. 6, 8 and 17 are clearly excellent in every respect.

EXAMPLE 3

Each 0.01 mole of the present couplers indicated in the following Table 3 and the above control couplers A and B and the following control coupler D was added to a mixture of the same weight of tricresyl phosphate and 3 times volume of ethyl acetate and the resulting mixture was heated to 60° C. to form a complete solution. The solution was added to an aqueous solution of "Alkanol B" and gelatin, the resulting mixture was emulsified by a colloid mill to prepare each coupler dispersion.

Then, the coupler dispersion was added to a silver iodobromide emulsion (6 mole % silver iodide, containining 0.1 mole silver) and the mixture was coated onto a cellulose acetate film base and then dried to prepare 6 silver halide photosensitive materials for color photography having a stable coated film (Samples No. 13 to No. 18).

Control coupler D:

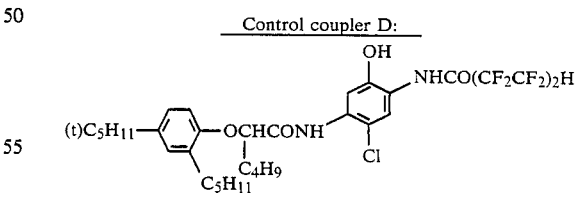

The sample was subjected to wedge exposure according to a conventional method and then treated as stated hereunder.

| (Treatment) | |
|---|---|
| Treatment step (33° C.) | Treatment time |
| Color development | 3 min. 15 sec. |
| Bleach | 6 min. 30 sec. |
| Water washing | 3 min. 15 sec. |
| Fixing | 6 min. 30 sec. |
| Water washing | 3 min. 15 sec. |

-continued

| Stabilization | 1 min. 30 sec. |
|---|---|
| (Color developing solution, composition) | |
| 4-Amino-3-methyl-N-ethyl-N- | 4.8 g. |
| (β-hydroxyethyl)aniline sulfate | |
| Anhydrous sodium sulfate | 0.14 g. |
| Hydroxylamine 1/8 sulfate | 1.98 g. |
| Sulfuric acid | 0.74 g. |
| Anhydrous potassium carbonate | 28.85 g. |
| Anhydrous potassium hydrogencarbonate | 3.46 g. |
| Anhydrous potassium sulfite | 5.10 g. |
| Potassium bromide | 1.16 g. |
| Sodium chloride | 0.14 g. |
| Nitriloacetic acid trisodium salt | 1.20 g. |
| Potassium hydroxide | 1.48 g. |
| Water to make up 1 l. | |
| (Bleaching solution, composition) | |
| Ethylenediaminetetraacetato iron ammonium complex | 100 g. |
| Ethylenediaminetetraacetato di-ammonium salt | 10 g. |
| Ammonium bromide | 150 g. |
| Glacial acetic acid | 10 ml. |
| Water to make up 1 l. | |
| Adjusted to pH 6.0 with aqueous ammonia | |
| (Fixer, composition) | |
| Ammonium thiosulfate | 175.0 g. |
| Anhydrous sodium sulfite | 8.6 g. |
| Sodium metasulfite | 2.3 g. |
| Water to make up 1 l. | |
| Adjusted to pH 6.0 with acetic acid | |
| (Stabilizer, composition) | |
| Formalin (37% aqueous solution) | 1.5 ml. |
| Konidax (manufactured by Konishiroku Photo Ind. Co., Ltd.) | 7.5 ml. |
| Water to make up 1 l. | |

The produced cyan color image was determined for photographic characteristics. The results are summarized in Table 3.

TABLE 3

| Sample No. | Coupler applied | Relative sensitivity | Maximum density |
|---|---|---|---|
| 13 | No. 1 | 95 | 2.03 |
| 14 | No. 5 | 96 | 2.10 |
| 15 | No. 8 | 100 | 2.20 |
| 16 | Control coupler A | 92 | 1.66 |
| 17 | Control coupler B | 85 | 1.55 |
| 18 | Control coupler D | 80 | 1.48 |

As apparent from the above Table 3, the samples using the present coupler are excellent in sensitivity and color development.

Also, the present sample, as a result of spectral measurement, has been found to show the absorption maximum in a long wave length range of a red region and sharpness in a short wave length range and thus produce a favourable dye image in color reproduction in a green region, as compared with the control coupler.

EXAMPLE 4

The samples No. 1 to No. 6 prepared in the above Example 1 were subjected to wedge exposure and then developed with the composition 1 in the Example 1. On the other hand, developing treatment was carried out with a bleach-fixing solution having the following composition to study discoloration of a cyan dye with an exhausted bleach-fixing solution.

| (Bleach-fixing solution, composition) | |
|---|---|
| Ethylenediaminetetraacetato iron ammonium complex | 50 g. |
| Ammonium sulfite (40% solution) | 50 ml. |
| Ammonium thiosulfate (70% solution) | 140 ml. |
| Aqueous ammonia (28% solution) | 20 ml. |
| Ethylenediaminetetraacetic acid | 4 g. |
| Hydrosulfite | 5 g. |
| Water to make up 1 l. | |

The sample thus treated was determined for reflection density of cyan dye. The results are summarized in Table 4. Dye residual rate at the maximum density is calculated from the following equation.

$$\text{Dye residual rate} = \frac{\text{Treatment with fresh bleach-fixing solution}}{\text{Treatment with exhausted bleach-fixing solution}} \times 100$$

TABLE 4

| Coupler applied | Fresh BF* treatment | Exhausted BF* treatment | Dye residual rate |
|---|---|---|---|
| No. 6 | 2.20 | 2.18 | 99 |
| No. 8 | 2.22 | 2.18 | 98 |
| No. 17 | 2.18 | 2.16 | 99 |
| Control coupler A | 2.15 | 1.35 | 63 |
| Control coupler B | 1.98 | 1.92 | 97 |
| Control coupler C | 1.80 | 1.75 | 97 |

*BF = Bleach-fixing solution

It can be seen from the Table 4 that the sample using the present coupler shows less discoloration in cyan dye when treated with exhausted bleach-fixing solution.

EXAMPLE 5

The samples prepared in the same manner as in the above Example 1 were tested for light fastness, heat fastness and moisture fastness. The results are summarized in Table 5.

TABLE 5

| | | Color development 1 | | | Color development 2 | | |
|---|---|---|---|---|---|---|---|
| Sample No. | Coupler applied | light fastness | heat fastness | moisture fastness | light fastness | heat fastness | moisture fastness |
| 19 | No. 20 | 85 | 98 | 97 | 86 | 98 | 98 |
| 20 | No. 21 | 86 | 98 | 98 | 87 | 98 | 98 |
| 21 | No. 25 | 86 | 98 | 97 | 86 | 97 | 97 |
| 22 | Control coupler A | 85 | 45 | 60 | 86 | 46 | 62 |
| 23 | Control coupler B | 61 | 95 | 93 | 57 | 96 | 95 |
| 24 | Control coupler C | 55 | 94 | 92 | 52 | 95 | 93 |

In the above Table 5, light fastness, moisture fastness and heat fastness are represented in the same manner as in the above Table 2.

As can be seen from the above Table 5, the control couplers A, B and C are evaluated as in the Table 2. On the other hand, the present couplers Nos. 20, 21 and 25 are clearly excellent in every respect.

EXAMPLE 6

The same procedures as in the above Example 3 were repeated except that the present couplers indicated in Table 6 were instead employed, thereby producing 6 silver halide photosensitive materials for color photography (Samples Nos. 25 to 30).

The sample was exposed and treated in the same manner as in the above Example 3.

The produced cyan color image was determined for photographic characteristics. The results are summarized in Table 6.

TABLE 6

| Sample No. | Coupler applied | Relative sensitivity | Maximum density |
|---|---|---|---|
| 25 | No. 24 | 98 | 2.05 |
| 26 | No. 28 | 100 | 2.20 |
| 27 | No. 40 | 100 | 2.09 |
| 28 | Control coupler A | 100 | 1.67 |
| 29 | Control coupler B | 93 | 1.68 |
| 30 | Control coupler D | 80 | 1.53 |

As is apparent from the above Table 6, the samples using the present coupler are excellent in sensitivity and color development.

Also, the present sample, as a result of spectral measurement, has been found to show the absorption maximum in a long wave length range of a red region and sharpness in a short wave length range and thus produce a favourable dye image in color reproduction in a green region, as compared with the control coupler.

EXAMPLE 7

The samples No. 19 to No. 24 as prepared in the above Example 5 were exposed, treated and tested for cyan dye maximum reflection density in the same manner as in the above Example 4. The results are summarized in Table 7.

TABLE 7

| Coupler applied | Fresh BF treatment | Exhausted BF treatment | Dye residual rate |
|---|---|---|---|
| No. 20 | 2.19 | 2.19 | 100 |
| No. 21 | 2.17 | 2.15 | 99 |
| No. 25 | 2.17 | 2.17 | 100 |
| Control coupler A | 2.18 | 1.37 | 63 |
| Control coupler B | 1.90 | 1.84 | 97 |
| Control coupler C | 1.80 | 1.73 | 96 |

It can be seen from the above Table 7 that the samples using the present coupler show less discoloration of cyan dye when treated with exhausted bleach-fixing solution.

EXAMPLE 8

The samples prepared in the same manner as in the above Example 1 were tested for light fastness, heat fastness and moisture fastness. The results are summarized in Table 8.

TABLE 8

| Sample No. | Coupler applied | Color development 1 | | | Color development 2 | | |
|---|---|---|---|---|---|---|---|
| | | light fastness | heat fastness | moisture fastness | light fastness | heat fastness | moisture fastness |
| 31 | No. 44 | 86 | 98 | 96 | 87 | 98 | 99 |
| 32 | No. 45 | 85 | 97 | 97 | 86 | 100 | 100 |
| 33 | No. 50 | 85 | 98 | 97 | 85 | 97 | 96 |
| 34 | Control coupler A | 84 | 47 | 63 | 85 | 46 | 63 |
| 35 | Control coupler B | 60 | 94 | 92 | 56 | 95 | 92 |
| 36 | Control coupler C | 57 | 93 | 91 | 50 | 94 | 90 |

In the above Table 8, light fastness, moisture fastness and heat fastness are represented in the same manner as in the above Table 2.

The present couplers No. 44, No. 45 and No. 50 have been found to show excellent properties in every respect.

EXAMPLE 9

The same procedures and materials as in the above Example 3 were repeatedly employed except that the present couplers indicated in Table 9 were used, thereby producing 6 silver halide photosensitive materials for color photography (Samples No. 37 to No. 42).

The sample was exposed, treated in the same manner as in the above Example 3.

The cyan color image was determined for photographic characteristics. The results are summarized in Table 9.

TABLE 9

| Sample No. | Coupler applied | Relative sensitivity | Maximum density |
|---|---|---|---|
| 37 | No. 50 | 97 | 2.18 |
| 38 | No. 57 | 100 | 2.22 |
| 39 | No. 64 | 100 | 2.20 |
| 40 | Control coupler A | 100 | 1.67 |
| 41 | Control coupler B | 92 | 1.61 |
| 42 | Control coupler D | 81 | 1.50 |

As apparent from the above Table 9, the samples using the present coupler are excellent in sensitivity and color development. Also, the present samples have been found to produce a favourable dye image in color reproduction in a green region similarly to those in Example 3.

EXAMPLE 10

The samples No. 31 to No. 33 prepared in the above Example 8 were exposed, treated and tested for cyan dye maximum reflection density in the same manner as in the above Example 4. The results are summarized in Table 10.

TABLE 10

| Coupler applied | Fresh BF treatment | Exhausted BF treatment | Dye residual rate |
|---|---|---|---|
| No. 44 | 2.18 | 2.18 | 100 |
| No. 45 | 2.22 | 2.20 | 99 |
| No. 50 | 2.18 | 2.18 | 100 |
| Control coupler A | 2.16 | 1.38 | 64 |
| Control coupler B | 1.90 | 1.86 | 98 |
| Control coupler C | 1.82 | 1.75 | 96 |

It can be seen from the above Table 10 that the samples using the present coupler show less discoloration of cyan dye when treated with exhausted bleach-fixing solution.

EXAMPLE 11

The couplers of the present invention, the above-mentioned Control coupler D and the below-mentioned Control couplers E and F as shown in Table 11 were prepared, exposed and then developed in the same manner as in Example 9 to obtain Samples (Sample Nos. 43 to 49). The thus obtained Samples were tested for light fastness, heat fastness and moisture fastness of the cyan dye image. The results are shown in Table 11.

TABLE 11

| Sample No. | Coupler applied | light fastness | heat fastness | moisture fastness |
|---|---|---|---|---|
| 43 | No. 49 | 83 | 96 | 97 |
| 44 | No. 59 | 82 | 95 | 95 |
| 45 | No. 67 | 86 | 99 | 98 |
| 46 | No. 81 | 88 | 96 | 98 |
| 47 | Control coupler D | 56 | 82 | 88 |
| 48 | Control coupler E | 68 | 79 | 85 |
| 49 | Control coupler F | 82 | 90 | 94 |

Control coupler E:

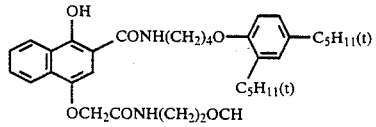

Control coupler F:

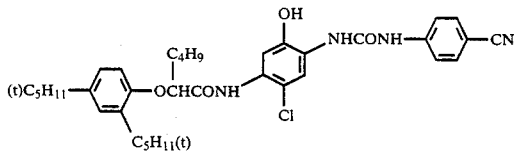

As seen from Table 11, it can be understood that the Samples obtained by using the cyan couplers according to the present invention exhibit excellent properties in all the points of light fastness, heat fastness and moisture fastness.

EXAMPLE 12

With respect to the Samples obtained in the same manner as in Example 1 except that the couplers shown in Table 12 were used, photographic properties were measured according to the same procedures as in Example 1. The results are shown in Table 12.

TABLE 12

| Sample No. | Coupler applied | Color development 1 | | Color development 2 | |
|---|---|---|---|---|---|
| | | Relative sensitivity | Maximum density | Relative sensitivity | Maximum density |
| 50 | 20 | 100 | 2.20 | 72 | 1.83 |
| 51 | 21 | 100 | 2.18 | 72 | 1.82 |
| 52 | 25 | 99 | 2.18 | 70 | 1.80 |

EXAMPLE 13

With respect to the Samples obtained in the same manner as in Example 1 except that the couplers shown in Table 13 were used, photographic properties were measured according to the same procedures as in Example 1. The results are shown in Table 13.

TABLE 13

| Sample No. | Coupler applied | Color development 1 | | Color development 2 | |
|---|---|---|---|---|---|
| | | Relative sensitivity | Maximum density | Relative sensitivity | Maximum density |
| 53 | 44 | 100 | 2.18 | 72 | 1.80 |
| 54 | 45 | 100 | 2.20 | 74 | 1.83 |
| 55 | 50 | 99 | 2.19 | 71 | 1.80 |

We claim:

1. A silver halide color photosensitive material for color photography which comprises a phenol type cyan coupler having the formula:

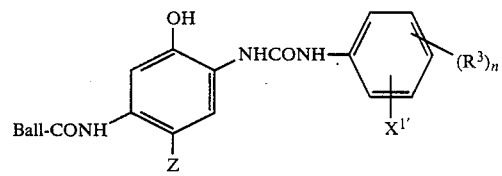

wherein
R$^3$ is a hydrogen atom, a halogen atom, a hydroxy group, a nitro group, or a monovalent organic group;
X$^{1'}$ is —COOR$^1$, —COR$^1$, —SO$_2$OR$^1$,

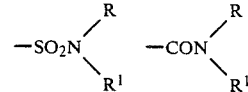

—NO$_2$ or —CF$_3$, in which R is a hydrogen atom, an alkyl group or an aryl group and R$^1$ is an alkyl group or an aryl group;
Z is a hydrogen atom or a removable group upon a coupling reaction with an oxidized product of a color developing agent:
n is 0 to 3; and
Ball has the formula:

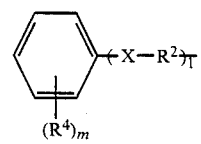

wherein

X is an oxygen atom or a sulfur atom;

R⁴ is a group selected from the group consisting of a hydrogen atom, a halogen atom, an alkyl group, an aryl group, a heterocyclic group, an aralkyl group, an alkoxy group, an aryloxy group, a hydroxy group, an acyloxy group, a carboxy group, an alkoxycarbonyl group, an aryloxycarbonyl group, a mercapto group, an alkylthio group, an arylthio group, an alkylsulfonyl group, an arylsulfonyl group, an acyl group, an acylamino group, a sulfonamido group, a carbamoyl group and a sulfamoyl group;

$R^2$ is a straight or branched alkylene group;

m is 1 to 4; and l is 0 or 1.

2. The silver halide color photosensitive material of claim 1, wherein X is an oxygen atom.

3. The silver halide color photosensitive material of claim 1, wherein $R^4$ is an alkyl group.

4. The silver halide color photosensitive material of claim 1, wherein Z is selected from the group consisting of a halogen atom, a carbamoyloxy group, a carbamoylmethoxy group, an acyloxy group, a sulfonamido group, and a succinimido group.

5. A silver halide color photosensitive material for color photography which comprises a phenol type cyan coupler having the formula:

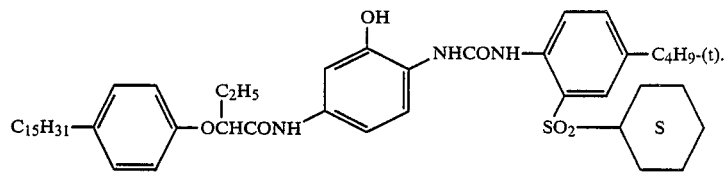

* * * * *